(12) United States Patent
Lacroix et al.

(10) Patent No.: US 8,871,182 B2
(45) Date of Patent: Oct. 28, 2014

(54) 3D NANOCRYSTALS AND MANUFACTURING METHODS

(75) Inventors: Christophe Jan Lacroix, Kilchberg (CH); Christophe Chassard, Zurich (CH); Marcus Yaffee, Hinteregg (CH)

(73) Assignee: Eth Zurich, Zurich (CH)

( * ) Notice: Subject to any disclaimer, the term of this patent is extended or adjusted under 35 U.S.C. 154(b) by 0 days.

(21) Appl. No.: 13/697,395

(22) PCT Filed: May 11, 2011

(86) PCT No.: PCT/CH2011/000111
§ 371 (c)(1),
(2), (4) Date: Nov. 12, 2012

(87) PCT Pub. No.: WO2011/140668
PCT Pub. Date: Nov. 17, 2011

(65) Prior Publication Data
US 2013/0058870 A1 Mar. 7, 2013

(30) Foreign Application Priority Data
May 12, 2010 (WO) ................ PCT/CH2010/000128

(51) Int. Cl.
| | |
|---|---|
| A61K 49/00 | (2006.01) |
| A61K 9/00 | (2006.01) |
| A61K 49/06 | (2006.01) |
| B32B 5/16 | (2006.01) |
| C04B 35/04 | (2006.01) |
| C09K 3/00 | (2006.01) |
| A61B 5/055 | (2006.01) |
| C30B 29/52 | (2006.01) |
| C30B 7/00 | (2006.01) |
| C30B 29/02 | (2006.01) |
| C30B 29/60 | (2006.01) |
| B82Y 30/00 | (2011.01) |

(52) U.S. Cl.
CPC . *C30B 7/00* (2013.01); *C30B 29/52* (2013.01); *C30B 29/02* (2013.01); *C30B 29/60* (2013.01); *B82Y 30/00* (2013.01)
USPC ............. 424/9.3; 424/9.1; 424/400; 428/402; 252/62.54; 252/182.32

(58) Field of Classification Search
None
See application file for complete search history.

(56) References Cited

U.S. PATENT DOCUMENTS

| | | | | |
|---|---|---|---|---|
| 6,268,041 | B1* | 7/2001 | Goldstein ...................... | 428/208 |
| 7,037,574 | B2* | 5/2006 | Paranjpe et al. .............. | 428/200 |
| 2002/0106813 | A1* | 8/2002 | Smith et al. ................... | 436/180 |
| 2006/0059948 | A1* | 3/2006 | Sato et al. ..................... | 65/32.1 |
| 2009/0225310 | A1* | 9/2009 | Yang et al. .................... | 356/301 |

OTHER PUBLICATIONS

Tao, A, R., et al., "Shape Control of Colloidal Metal Nanocrystals", 2008, Small, pp. 310-325.*
Ostraat, M.L., et al., "Ultraclean Two-Stage Aerosol Reactor for Production of Oxide-Passivated Silicon Nanoparticles for Novel Memory Devices" 2001, JES, pp. G265-G270.*
International Search Report for corresponding International Application No. PCT/CH2011/000111 mailed Jun. 28, 2011.
Mayoral et al., "Polyhedral shaped gold nanoparticles with outstanding near-infrared light absorption", Applied Physics A; Materials Science & Processing, Jul. 2009, vol. 97, No. 1, pp. 11-18.
Sanchez-Iglesias et al., "Rapid Epitaxial Growth of Ag on Au Nanoparticles: From Au Nanorods to Core-Shell Au@Ag Octahedrons", Chemistry, A European Journal, Apr. 2010, vol. 16, No. 19, pp. 5558-5563.
Huang et al., "Synthesis and characterization of Au core-Au—Ag shell nanoparticles from gold seeds: Impacts of glycine concentration and pH", Journal of Colloid and Interface Science, Sep. 2006, vol. 301, No. 1, pp. 145-154.
Mednikov et al., "Nanosized $Au_4Pd_{32}(CO)_{28}(PMe_3)_{14}$ Containing a Highly Distorted Encapsulated $Au_4$ Tetrahedron: Proposed Multi-Twinned Growth-Pattern from Two Deformed Au-Centered Double Icosahedral-Based Fragments*", Journal of Cluster Science, Jun. 2005, vol. 16, No. 2, pp. 287-302.
Seo et al., "Polyhedral Gold Nanocrystals with $O_h$ Symmetry: From Octahedra to Cubes", Journal of the American Chemical Society, Nov. 2006, vol. 128, No. 46, pp. 14863-14870.
Xu et al., "FeCo—Au core-shell nanocrystals", Applied Physics Letters, 2007, vol. 91, pp. 233107-1-233107-3.
Bao et al., "Formation Mechanism and Shape Control of Monodisperse Magnetic $CoFe_2O_4$ Nanocrystals", Chemistry of Materials, 2009, vol. 21, pp. 3458-3468.
Millstone et al., "Colloidal Gold and Silver Triangular Nanoprisms", Small Journal, 2009, vol. 5, No. 6, pp. 646-664.
Whetten et al., "Nano-Golden Order", Science Magazine, Oct. 2007, vol. 318, pp. 407-408.
Groman et al., "Ultrasmall Mixed Ferrite Colloids as Multidimensional Magnetic Resonance Imaging, Cell Labeling, and Cell Sorting Agents", Bioconjugate Chem., 2007, vol. 18, pp. 1763-1771.
Huo et al., "Polymer Pen Lithography", Science Magazine, Sep. 2008, vol. 321, pp. 658-660.
King et al., "Structure and Bonding in the Omnicapped Truncated Tetrahedral $Au_{20}$ Cluster: Analogies between Gold and Carbon Cluster Chemistry", Inorganic Chemistry, 2004, vol. 43, No. 15, pp. 4564-4566.

(Continued)

*Primary Examiner* — Michael G Hartley
*Assistant Examiner* — Lance Rider
(74) *Attorney, Agent, or Firm* — Renner, Otto, Boisselle & Sklar, LLP (57) ABSTRACT

The invention relates to nanocrystals, containing one or more metals as defined in the specification; having a size of 2 to 200 nm; having a defined, three-dimensional polyhedral structure, optionally functionalized by ligands and/or embedded crystals. The invention further relates to monodisperse assemblies of such nanocrystals, to formulations and devices comprising such nanocrystals as well as to the manufacture and use thereof.

4 Claims, 4 Drawing Sheets

(56) References Cited

OTHER PUBLICATIONS

Liu et al., "The Controlled Evolution of a Polymer Single Crystal", Science Magazine, Mar. 2005, vol. 307, pp. 1763-1766.

Lopez-Acevedo et al., "Structure and Boning in the Ubiquitous Icosahedral Metallic Gold Cluster $Au_{144}(SR)_{60}$", The Journal of Physical Chemistry C Letters, 2009, vol. 113, pp. 5035-5038.

Norris et al., "Doped Nanocrystals" Science Magazine, Mar. 2008, vol. 319, pp. 776-779.

Li et al., "$Au_{20}$: A Tetrahedral Cluster", Science, vol. 299, Feb. 7, 2003, pp. 864-867.

Fan et al., "Self-Assembly of Ordered, Robust, Three-Dimensional Gold Nanocrystal/Silica Arrays", Science, vol. 304, Apr. 23, 2004, pp. 567-571.

Gruene et al., "Structures of Neutral $Au_7$, $Au_{19}$, and $Au_{20}$ Clusters in the Gas Phase", Science, vol. 321, Aug. 1, 2008, pp. 674-676.

Jadzinsky et al., "Structure of a Thiol Monolayer-Protected Gold Nanoparticle at 1.1 Å Resolution", Science, vol. 318, Oct. 19, 2007, pp. 430-433.

Yin et al., "Colloidal nanocrystal synthesis and the organic-inorganic interface", Nature, vol. 437, Sep. 27, 2005, pp. 664-670.

* cited by examiner

3D NANOCRYSTALS AND MANUFACTURING METHODS

This application is a national phase of International Application No. PCT/CH2011/000111 filed May 11, 2011, and published in the English language which claims priority to PCT/CH2010/000128 filed May 12, 2012.

The invention relates to nanocrystals, containing one or more metals; having a size of 2 to 200 nm; having a defined, three-dimensional (3D) polyhedral structure, optionally functionalized by ligands and/or embedded crystals. The invention further relates to monodisperse assemblies of such nanocrystals, to formulations and devices comprising such nanocrystals as well as to the manufacture and use thereof.

Nanocrystalline materials and supraatomic metal clusters ($10^2$-$10^5$ atoms) are known and described extensively in literature. Such materials find applications in a wide range of technological applications, such as in the field of material science and in the field of biomedical applications.

The materials known so far are two-dimensional (2D) crystals, or degenerate structures that do not exhibit a well defined regular 3D geometry. Further, the materials known, often lack stability.

Xu et al. (Applied Phys. Letters 2007, 91, 233107) describe cubic FeCo—Au core shell nanocrystals and methods of manufacturing thereof; the document suggests its use in biomedical applications. The nanocrystals disclosed therein are "heterostructured" particles exhibiting no interior crystalline metal lattices, rather displaying an undefined mixed alloy in an undefined structure. Further, these particles are mixed in size, i.e. not monodisperse as defined herein. It is believed that these structural differences are due to an alternative manufacturing process (condensed from the gas phase, not an LPSP process as defined herein).

Bao et al. (Chem. Mater. 2009, 32, 3458 ff) describe CoFe2O4 nanocrystals and large scale synthesis thereof. The manocrystals disclosed therein are not 3D isotropic cubes or regular polyhedra. The document states some structures are nanocubes but there are no crystalline diffractions seen and data presented support a degenerate 2D geometry (i.e., partial lattice fringes visible in a small fraction of images). "Corners" of cubes are rounded or display "intermediate morphologies" that remain ill-defined. The document presents structural interpretations of TEM images of particles adsorbed on a thin carbon film substrate that are inconsistent with the methodology applied, i.e., electron density and lattice-fringe overlap are consistent with flat particles. In conclusion, the document is self-contradictory and does not disclose crystals of a defined, 3D polyhedral structure.

Millstone et al. (small 2009, no. 6, 646 ff) describe trigonal Au and Ag nanoprisms, and compare various manufacturing methods thereof. The nanoprisms disclosed therein are degenerate structures or unstable under environmental conditions or application specific stresses, e.g., high voltage (5 kV). Triangular nanoprisms disclosed are not isotropic (i.e., all vertices equal edge lengths in three dimensions). Further, the nanoprisms disclosed are metal-ligand structures and not metal-metal bonded. It is believed that these structural differences are due to an alternative manufacturing process (not an LPSP process as described herein). The document further concludes that "understanding how to predict and control nanoparticle size and shape remains a critical step in the wide spread use of noble metal nanoparticles in applications".

Mayoral et al. (Appl. Phys. A (2009) 97: 11-18) describe polyhedral Au nanocrystals and methods of manufacturing thereof; the document suggests its use in cancer diagnosis and treatment. The nanocrystals disclosed therein exhibit "two main morpohologies", suggesting an undefined structure. Furthermore, these particles are mixed in size, i.e. not monodisperse as defined herein. It is believed that these structural differences are due to an alternative manufacturing process; seed-mediated growth from an aqueous solution, not an LPSP process as defined herein.

Sanchez-Iglesias et al. (Chem. Eur. J. (2010) 16: 5558-5563) describe Ag, Au Au@Ag nanocrystals and methods of manufacturing thereof. The nanocrystals disclosed therein do not exhibit a defined 3D polyhedral structure. Particularly, FIGS. 2a, 2c, 2e and 3 show an ill-defined morphology of the nanocrystals obtained. Further, FIG. 4 provides an explanation why such ill-defined structures are obtained in the process disclosed therein.

Huang et al. (J. of Colloid and Interface Science (2006) 301: 1145-154) describe Au and Au@Ag nanocrystals and methods of manufacturing thereof; the document suggests its use in information technology, optoelectronics and sensing. The nanocrystals disclosed therein exhibit dumbbell-shaped and peanut-shaped morpohologies, suggesting an undefined structure. Further, these particles are mixed in size, i.e. not monodisperse as defined herein. It is believed that these structural differences are due to an alternative manufacturing process; seeded-growth from an aqueous solution, not an LPSP process as defined herein.

Mednikov et al. (J. of Cluster Science (2005)16: 287-302) describe Au—Pd clusters and methods of manufacturing thereof. The clusters disclosed therein are less than one nanometer. The authors describe the structures as "highly distorted double icosahedral atom arrangement", and are therefore neither nanocrystals nor having a defined polyhedral structure.

Seo et al. (JACS (2006) 128: 14863-14870) describe polyhedral Au Nanocrystals uniform in shape and size and methods of manufacturing thereof. As acknowledged by the authors, the nanocrystals exhibit nearly octahedron fashion with rounded apexes. Again, it is believed that these structural differences are due to an alternative manufacturing process; seeded-growth from an aqueous solution, not an LPSP process as defined herein.

Consequently, it is an object of the present invention to provide improved nanocrystals and to mitigate at least some of the drawbacks of the state of the art. In particular, it is an aim of the present invention to provide nanocrystals and methods of manufacturing thereof suitable for use in the field of material science and/or in the field of biomedical applications.

These objectives are achieved by nanocrystals as defined in claim 1. Further aspects of the invention are disclosed in the specification and independent claims, preferred embodiments are disclosed in the specification and the dependent claims.

The present invention will be described in more detail below. It is understood that the various embodiments, preferences and ranges may be combined at will. Further, depending on the specific embodiment, selected definitions, embodiments or ranges may not apply.

Unless otherwise stated, the following definitions shall apply in this specification:

The term "containing" shall, in the context of this invention, also include the meaning of comprising or consisting of.

The term "nanocrystal" is known in the field. It particularly denotes Supraatomic Metal Clusters [SMC], exhibiting reflection planes corresponding directly to geometrically well-defined three-dimensional polyhedral structures. This definition excludes crystals, unstable or degenerate structures or so-called "nanocrystals" that do not exhibit a well-defined regular 3D geometry. The term "polyhedral structure" is known in the field. It particularly denotes a geometric solid in three dimensions with flat faces and straight edges. The present invention particularly relates to nanocrystals which are n-gonal pyramids with a polyhedral base such as tetrahedra or hexagonal pyramids.

The term "ligand" is known in the field. It particularly denotes an entity (ion or molecule) that directly binds to a central metal-atom to form a coordination complex. The bonding between metal and ligand generally involves formal donation of one or more of the ligands electron pairs and ranges from covalent to ionic. The term "ligand" includes both, non-metal ligands on the surface and bridging-ligands (e.g., O, S, N, H, common to metal chemistry). In coordination chemistry, the ligands that are directly bond to the metal (i.e. share electrons), form part of the first coordination sphere and are sometimes called "inner sphere" ligands. Accordingly, "outer-sphere" ligands are not directly attached to the metal, but are bonded, generally weakly, to the first coordination shell. In the context of the present invention, only an "inner sphere ligand" is considered a "ligand". It is accepted that metals and metalloids are bound to ligands in virtually all circumstances (with the exception of gaseous "naked" metal ions that have been generated in the vapor phase under high vacuum) prior to the processes disclosed herein.

The term "Vapor phase ballast" ("VPB") is known in the field. It particularly denotes the extended headspace created by a similar volume of reactants kept at similar physical conditions. Such VPB balances potential fluctuations in vapor pressure during synthetic stages throughout the reaction environment. Typically, a "similar volume" is within +/−90%, such as +/−20% most preferably +/−5% of the reaction volume. Typically, similar physical conditions (particularly temperature and pressure) are within a range of +/−20%, preferably +/−10%, much preferably +/−5% of the conditions in the reaction vessel.

The term "monodisperse" is known in the field. In the context of the present invention, it particularly denotes an assembly of nanocrystals according to the invention that have the same size and shape. Whereby the "same size" is defined as 95% (n/n), preferably 99% (n/n) of the naocrystals are within ±10%, preferably ±2%, of the size as reported in nanometers and whereby the "same shape" is defined as 99% or more of the nanocrystals present show the same polyhedral structure. For example, nanocrystals are considered monodisperse, with individual sols exhibiting 40 nm±1 nm for example. (Note: Size distribution variance includes instrumental measuring tolerance of the microscope, 0.5 nm.)

The present invention will be better understood by reference to the figures:

FIG. 5 shows an EPR spectral series tracking sequential layering and composition of mixed metal complexes through synthetic progression of nanocrystal composites. The spectra clearly display the evolution of defined and elevated ferromagnetic and superparamagnetic properties of the materials. Surface charge, ligand coupling and magnetic properties of transition metal complexes can be characterized in solution with EPR spectra. Serial EPR analysis demonstrates the absolute reduced surface and core properties of mixed FeCo@Au core shells through preliminary baseline 5a of Au atomic cores, the sequential layering of Co 5b and Fe 5c while maintaining a 0/null baseline throughout. Functional paramagnetic splitting visible in 5d is traced for the inventive nanocrystals (large signals) and is compared to the superparamagnetic signal of state-of-the-art ZnSe nanoparticles (minor signals).

FIG. 6 shows an experimental set-up useful for the manufacturing of the inventive crystals, whereby the abbreviations have the following meaning:
(R) Reaction vessel with Glass rotor
(V) Vapor Phase Ballast
(G1)-(G5) Gated manometers
(Ar) Argon
(VAC) Vacuum, maintained by a dry turbomolecular pumping system
(M) Motor
(I1)-(I2) Injectors
(T) Liquid nitrogen trap

In a first aspect, the invention relates to pure nanocrystals, i.e. nanocrystals, (a) containing (i.e. comprising or consisting of) one or more metals; (b) having a size of 2 to 200 nm; and (c) having a defined, three-dimensional polyhedral structure. This aspect of the invention is explained in further detail below:

It was surprisingly found that the inventive particles, when manufactured according to the process described herein, have a well defined polyhedral geometry (in the sense that they are essentially free of or free of lattice defects) and are pure (in the sense that essentially no or no surface ligands are bound to the nanocrystals and essentially no or no undefined elements are within the crystal structure). The inventive nanocrystals exhibit, depending on the elements selected, elevated magnetic, fluorescent and/or visible signals. These nanocrystals are thus improved over known nanocrystals, making them particularly suitable for a wide range of applications in the biomedical field and in materials science.

The inventive pure crystals may be considered as non-functionalized crystals, contrary to the mixed nanocrystals and capped nanocrystals described below.

Metals:

The inventive nanocrystals contain one or more, advantageously one or two, metals. The term metals is used in a broad sense and includes the elements of the groups 1-12 of the periodic table of elements as well as metals and semi-metals of groups 13-17. This includes alkali metals, alkali earth metals, "transition metals" (3d, 4d, 5d metals), "rare earth metals" (4f, 5f metals) and the following elements from groups 13-17: Al, Ga, In, Tl, Ge, Sn, Pb, As, Sb, Bi, Te, Po, At. In one embodiment, the elements are selected from the group of elements of the groups 3-12 of the periodic table of elements. Advantageously, the elements are selected from the group consisting of Fe, Au, Eu, Co, Cu, Os, Pt, Ag, Se.

As outlined, the inventive crystals may consist of either one element only, e.g. Au, or they may consist of two or more elements, e.g. FeCo. In the latter case, the elements are arranged like in an alloy type and are still considered "pure". This is to be distinguished from the "mixed" nanocrystals described below.

The inventive particles of this aspect of the invention are "pure", i.e. do not contain ligands bound to the surface or other material within the crystal structure. Thus, the invention relates to nanocrystals as described herein essentially consisting of, or consisting of, one or more elements of the groups 1-12, preferably 3-12, of the periodic table of elements.

Size of Nanocrystals:

The inventive nanocrystals are characterized by their size, determined as the largest diameter of the crystal by microscopy. This size is in the range of 2-200 nm, preferably in the range of 4-100 nm. Alternatively or additionally, inventive nanocrystals may be determined by the number of atoms present, which is in the range of $10^2$-$10^6$ atoms, preferably $10^3$-$10^5$ atoms.

The invention provides an LPSP process (as described below) which results not in the formation of one single nanocrystal but in the formation of an assembly of nanocrystals. It was surprisingly found that the nanocrystals, when manufactured as described herein, show a very narrow size distribution, they are considered monodisperse. Consequently, the invention also relates to an assembly of nanocrystals, such as an aqueous suspension containing nanocrystals as defined herein. The invention further relates to a monodisperse assembly of nanocrystals as defined herein. Typically, such assembly comprises $10^5$, preferably $10^6$ or more nanocrystals.

Structure:

The inventive nanocrystals are characterized by their 3D geometry [shape]. These shapes may be generally described as polyhedra; e.g., Platonic solids, pyramids which includes the following Bravais-lattices FCC, HCP and BCC. The inventive material may be thus also described as supraatomic crystalline material exhibiting a Bravais-lattice selected from the group consisting of FCC, HCP and BCC. Advantageously, the inventive crystals possess a tetragonal pyramidal or hexagonal pyramidal structure.

In an advantageous embodiment, the inventive nanocrystals are electron-dense. Consequently, the present invention also comprises nanocrystals that are not hollow and/or electron-dense.

In a second aspect, the invention relates to mixed nanocrystals, i.e. nanocrystals that contain one or more inner nanocrystals surrounded by an outer nanocrystal, whereby said inner nanocrystal(s)

a) contain one or more metals as defined herein;
b) have a size of 1 to 100 nm;
c) have a defined, three-dimensional polyhedral structure and whereby said outer nanocrystal
a) contains one or more metals as defined herein;
b) has a size of 3 to 200 nm;
c) has a defined, three-dimensional polyhedral structure and whereby the metals of inner and outer crystal differ. In addition to the above, this aspect of the invention shall be explained in further detail below:

It was surprisingly found that such mixed crystals may combine advantageous properties of different metals, such as magnetic properties for the inner nanocrystals with inert properties for the outer nanocrystals.

The inventive mixed crystals may be considered as internally functionalized crystals, contrary to the capped nanocrystals described below. In this aspect, the invention provides nanocrystals consisting of one or more inner nanocrystals embedded in an outer nanocrystal.

It is apparent, that the mixed nanocrystals as defined herein have a crystal-in-crystal structure (in literature also referred to as core-shell structure); the inner crystal(s) (the core) is/are "fixed". This distinguishes the inventive mixed nanocrystals from interstitial compounds: In interstitial compounds, an atom is located within a crystal structure, in the inventive mixed crystals, a crystal is located within a crystal. Mixed nanocrystals thus typically retain properties of both, the inner and the outer crystal, contrary to interstitial compounds.

It is also apparent that such mixed nanocrystals may contain either one inner crystal or more than one inner crystals. In an advantageous embodiment, said one or more inner crystal(s) are fully covered by said outer crystal.

Shape and size of mixed nanocrystals correspond to pure nanocrystals as defined above. Consequently, the invention also relates to an assembly of mixed nanocrystals, such as an aqueous suspension containing mixed nanocrystals as defined herein.

Metals:

The inventive nanocrystals contain two or more metals as defined herein, preferably metals selected from the group consisting of elements of the groups 1-12 (preferably: 3-12) of the periodic table of elements.

Advantageously, the metals are selected from the group consisting of (inner crystal@outer crystal) Fe@Au, Au@Fe, FeCo@Au, Au@FeCo, Gd@Fe, Gd@Au, Au@Eu, Au@Cu.

In a third aspect, the invention relates to capped nanocrystals, i.e. to pure or mixed nanocrystals as defined herein further containing ligands that partly or fully, preferably fully, cover the surface of said nanocrystals. In addition to the above, this aspect of the invention shall be explained in further detail below:

It was found that such capped nanocrystals may show improved physiological compatibility, which makes them suitable for biomedical applications.

The inventive capped nanocrystals may be considered as surface functionalized crystals, contrary to the mixed nanocrystals described above.

According to this aspect of the invention, the surface of the above described nanocrystals is functionalized with ligands, such as biochemically active ligands. This improves physiological compatibility, enables and/or facilitates binding to targeting molecules. Suitable ligands include ascorbates, citrates, tannins, carboxylic acids (such as fatty acids, lipoic acid dihydroxy lipoic acid (DHLA) and gallic acid), vitamins (such as vitamins A, E, C, D, B, K), proteins (such as Glutathione [GSH], amino acids, polymers (such as polyols). In specific embodiments, GSH and/or DHLA in reduced form are used as ligands. The ligands as described herein confer functional properties specific to each. Thus, capped nanocrystals as described herein show properties of the pure or mixed nanocrystals and of the ligands. Such capped nanocrystals are therefore suitable for a wide variety of applications, such as for diagnostic imaging with radiolabelled ligands.

Shape and size of capped nanocrystals correspond to pure nanocrystals as defined above. Consequently, the invention also relates to an assembly of capped nanocrystals, such as an aqueous suspension containing capped nanocrystals as defined herein.

In a fourth aspect, the invention relates to the manufacture of pure nanocrystals as described herein. Thus, the invention provides also a process for manufacturing pure nanocrystals as defined herein comprising the steps of a. Providing a reaction environment comprising a reaction vessel and a vapor phase ballast vessel connected thereto via the gas phase;
b. Providing a first solution ("solution A"), said solution comprising one or more metal precursors, solvent, optionally one or more reaction aids;
c. Providing a second solution ("solution B"), said solution comprising a reducing agent, solvent, optionally reaction aids
d. Providing a third solution ("solution C"), said solution comprising one or more metal precursors, solvent, optionally one or more reaction aids.
e. Filling the VPB vessel with solution C and the reaction vessel with solution A;
f. Adjusting the pressure of the reaction environment below atmospheric pressure;
g. Adding solution B to the reaction vessel;

whereby all steps are performed under ultra-clean conditions; and whereby the pressure is maintained below atmospheric pressure. Upon addition of solution B to the reaction vessel, the inventive pure nanocrystals are formed.

The manufacturing of nanocrystals in an aqueous solution is known, and may be performed according to the protocols of the documents identified above. However, the nanocrystals obtained according to these processes do not possess a defined polyhedral 3D crystal structure and/or are not pure in the sense that they contain ligands bound to the crystal surface and/or are not pure in the sense that they contain undefined elements within the crystal structure. These disadvantages may be overcome by following the manufacturing process as described herein. The inventive process may be described as a low-pressure solution phase [LPSP] synthetic process, as it is carried out below atmospheric pressure in solution (preferably: in an aqueous medium). It is understood that pre-synthetic process steps (i.e., cleaning and exhaustive purging with inert gas) as well as post-synthetic process steps (i.e. work up, derivatization) may take place at or above atmospheric pressure.

The process as set out in this aspect of the invention provides homogeneously sized, homogeneously shaped, nanocrystals of one or more elements selected from group 3-group 12 of the periodic table of elements. The process provided herein is high yielding and provides improved crystals (e.g. fluorescence, magnetism, stability) when compared with the prior art processes. The invention thus also provides a process as described herein characterized by a chemical yield >90 wt. %, preferably >95 wt. %, much preferably >99% of the inventive pure nanocrystals.

Further, the process as set out in this aspect of the invention provides nanocrystals having a shape that is seed-independent. This is in contrast to the prior art, where nanocrystals are obtained having a shape that is seed-dependent and/or seed-influenced.

Figure 6:
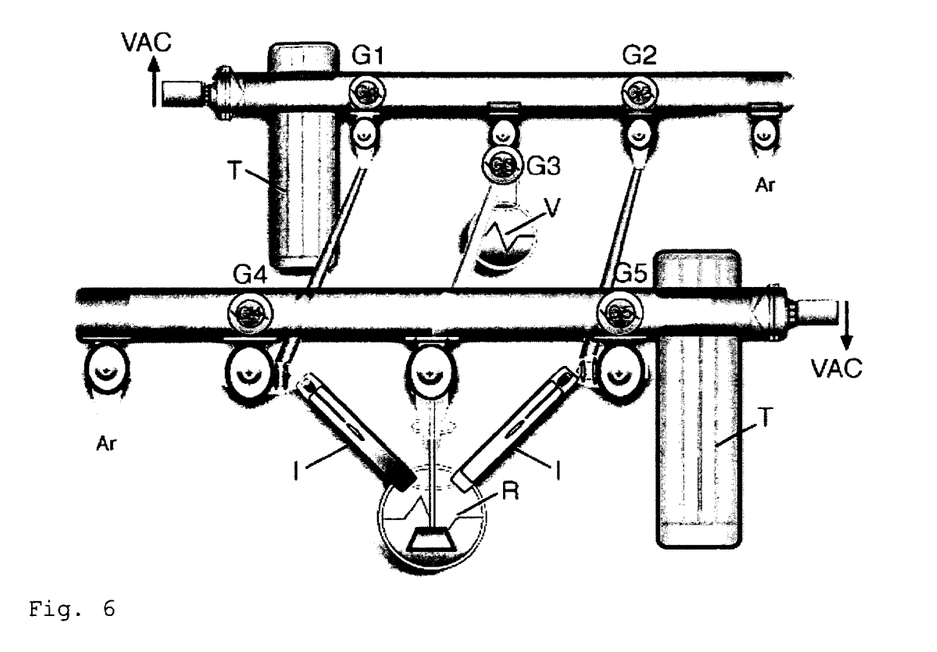
Figure 7:
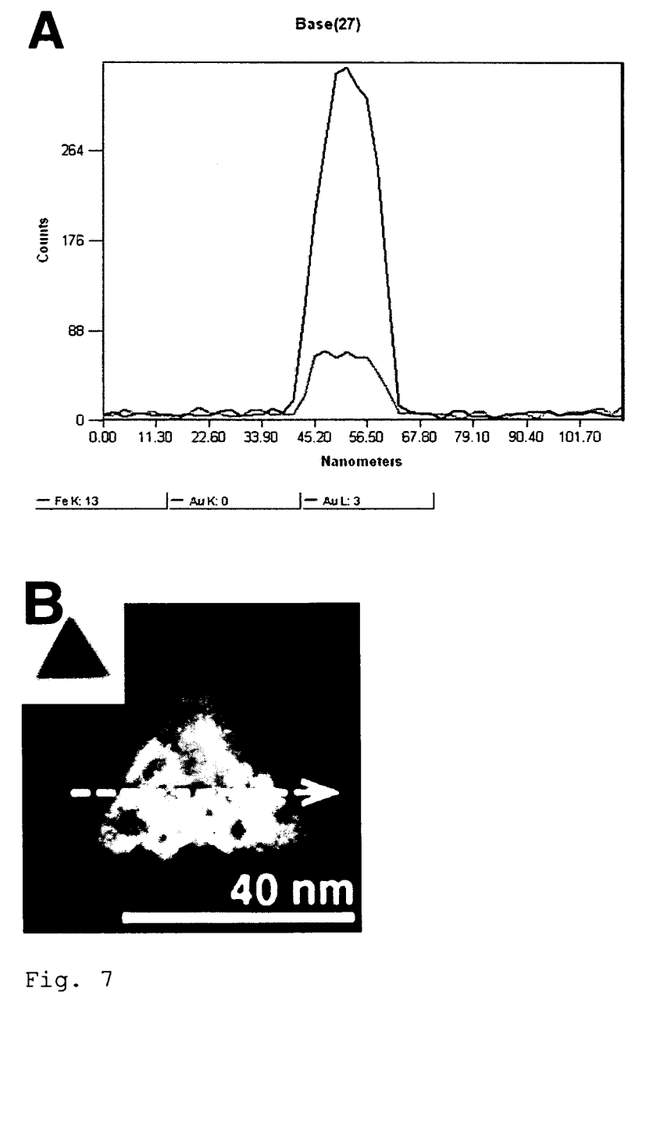
FIG. 7 shows an Ultra High Resolution Scanning Transmission Electron Microscopy X-ray Dispersive Spectra (UHR-STEM-XRDS) of inventive Au@Fe nanocrystals, where nanometers are given as X-axis and counts are given at Y-axis; the above graph shows AuK:0, the below graph shows FeK:13. Elemental analysis, graphed as a function of X-Y beam position relative to the scan reveals iron embedded deep within the pyramidal matrix of gold (7A). Material-dependent signals collected from multiple scans of mixed-metal Au@Fe C—C SMC (7B) yield quantitative elemental data in situ. UHR-STEM with an electron spot size calibrated to ≥2 Angstrom provides single counts of metal atoms across the width of individual particles (B insert). Morphology and composition of surface-derivatized particles remain constant under high-voltage.

This aspect of the invention shall be explained in further detail below:

Reaction Conditions:
Temperature: Typically, reaction takes place at temperatures between 0-100° C., preferably 25-80° C., such as room temperature.
Pressure: Typically, reaction takes place at pressures below atmospheric pressure, preferably below 1.3 mbar.
Ultra clean conditions: All exposed surfaces should be thoroughly cleaned. Glassware may be freshly etched with HF or charged Oxygen plasma prior to final triple distilled $H_2O$ wash. All vacuum lines and seals should be oil and grease free to $>1.3\times10^{-6}$ mbar. Starting materials are pure, as described in the experimental part.
Step a:
Reaction environment: In general, any equipment suited for ultra clean conditions may be employed. FIG. 6 shows a typical Schlenk-line set up, suitable for the manufacturing processes described herein. Advantageously, the equipment is made of glass or contains a glass-lining.
Reaction Vessel, Vapor Phase Ballast: known glassware may be used, such as Schlenk-type glassware. It is also possible to use manufacturing equipment that complies with the ultra-pure conditions as described herein, such as reactors with teflon- or glass coating.
Auxiliary devices: To maintain a reaction pressure below atmospheric pressure, a vacuum pump is attached to the reaction environment; particularly suitable are oil-free vacuum pumps. Auxiliary devices further include injectors to add reactants as described herein. Auxiliary devices further include measuring device to control the reaction.
Step b:
The starting materials for solution A are pure as described herein. Suitable solvents include water, such as three-times distilled water. Suitable metal precursors include any compound (or combinations thereof) containing metals as defined herein that are soluble in the solvent used. Particularly suitable are metal precursors ferrous gluconate hydrate, iron ammonium citrate, iron II and III chlorides, tetraaurochloric acid, cobalt chloride, platinum chloride. Suitable reaction aids include acids and/or bases.
Step c:
The starting materials for solution B are pure as described herein. Suitable solvents may be selected according to the reaction and include polar and non-polar solvents and combinations thereof. In an advantageous embodiment, water, such as three-times distilled water, is used. Suitable reaction aids include acids and/or bases. Suitable reducing agents include any compound (or combinations thereof) having a reduction potential to reduce the metal precursor to the corresponding metal. Particularly suitable reducing agent is a combination of GSH and di-hydroxy lipoic acid [DHLA].
Step d:
Solution C typically contains the same components as solution A, preferably in similar concentration (such as +/−20%; preferably +/−10% much preferred +/−2%). Typically, solution C and A are provided in similar amounts (such as +/−20%; preferably +/−10% much preferred +/−2%).
Step e:
An extended vapor phase headspace is created by bridging the reaction mixture with a similar volume of dissolved (particularly: aqueous) reactants. A consistent vacuum is maintained while balancing the vapor-phase gradient with back-pressure fed Argon.
Step f:
The reaction environment is evacuated at least twice to $10^{-2}$ mbar and purged with Argon gas to atmospheric pressure and then evacuated to $>10^{-1}$ mbar.

Step g:
Solution B is added in a manner known to the person skilled in the art. Thus, preferably solution A is stirred while B is added in a controlled manner to avoid boiling (rapid evaporation).

Work-Up:
In principle, it is possible to isolate the obtained pure nanocrystals using standard techniques. The isolated pure nanocrystals may be used in similar applications as corresponding known materials, e.g. as described below (8$^{th}$ aspect).

Alternatively, the obtained suspension containing pure nanocrystals may be used to prepare mixed nanocrystals as described below (e.g. according to the 5$^{th}$ aspect); to prepare capped nanocrystals as described below (e.g. according to the 6$^{th}$ aspect); to prepare a formulation or a device as described below (e.g. according to the 7$^{th}$ aspect).

In a fifth aspect, the invention relates to the manufacture of mixed metal nanocrystals as described herein.

Thus, the invention provides also a process for manufacturing mixed metal nanocrystals as defined herein comprising the steps of
a. Providing a reaction environment comprising a reaction vessel and a vapor phase ballast vessel connected thereto via the gas phase;
b. Providing a first solution ("solution A"), said solution comprising one or more metal precursors, solvent, optionally one or more reaction aids;
c. Providing a second solution ("solution B"), said solution comprising a reducing agent, solvent, optionally reaction aids and providing a suspension ("suspension D") said suspension comprising pure nanocrystals as defined herein, solvent, optionally one or more reaction aids;
d. Providing a third solution ("solution C"), said solution comprising one or more metal precursors, solvent, optionally one or more reaction aids.
e. Filling the VPB vessel with solution C and the reaction vessel with solution A;
f. Adjusting the pressure of the reaction environment below atmospheric pressure;
g. Adding solutions B and suspension D to the reaction vessel; whereby all steps are performed under ultra-clean conditions; and whereby the pressure is maintained below atmospheric pressure.

To obtain mixed nanocrystals, the principles of the above described LPSP process may be applied. This process is modified in that inner nanocrystals are synthesized first and added to a solution containing metal precursor that will form the outer crystal. Again, it is understood that pre-synthetic process steps (i.e., cleaning and exhaustive purging with inert gas) as well as post-synthetic process steps (i.e. work up, derivatization) may take place at or above 750 torr [100 kPa] under inert atmosphere.

The process as set out in this aspect of the invention provides homogeneously sized, homogeneously shaped, mixed nanocrystals as defined above (2$^{nd}$ aspect of the invention). The process provided herein is high yielding and provides improved crystals (e.g. fluorescence, magnetism, stability) when compared with the prior art processes. The invention thus also provides a process as described herein characterized by a chemical yield >90 wt. %, preferably >95 wt. %, much preferably >99% of the inventive mixed nanocrystals.

Again, the process as set out in this aspect of the invention provides nanocrystals having a shape that is seed-independent: the outside metal shape is not dependent on the interior metal. This is in contrast to the prior art, where such dependency is observed.

This aspect of the invention shall be explained in further detail below. Generally speaking, the manufacturing process of this embodiment differs from the previously described process in that an additional suspension D is provided in step c and added in step g:

Reaction Conditions:
Reaction conditions are similar to those according to the 4$^{th}$ aspect of the invention.

Step a:
Reaction environment: In general, the equipment used is similar to the equipment of the 4$^{th}$ aspect of the invention. For handling suspension D, additional equipment (such as an injector) is required.

Step b:
In general, step b is similar to step b described above, 4$^{th}$ aspect of the invention.

Step c:
In general, step c is similar to step b described above, 4$^{th}$ aspect of the invention. However, an additional suspension D, is provided. Suitable suspensions are those obtained according to the manufacturing process described above, 4$^{th}$ aspect of the invention.

Step d:
In general, step d is similar to step d described above, 4$^{th}$ aspect of the invention.

Step e:
In general, step e is similar to step e described above, 4$^{th}$ aspect of the invention.

Step f:
In general, step e is similar to step e described above, 4$^{th}$ aspect of the invention.

Step g:
Upon addition of solution B and suspension D to the reaction vessel, the inventive mixed nanocrystals are formed, whereby the nanocrystals of suspension D form said inner crystal(s) and the metal precursor of solution A forms said outer crystal. It was found advantageously to add both, B and D, simultaneously to the reaction vessel. It is understood that B and D are prepared and maintained separately until added to this step g.

Work-Up:
In principle, it is possible to isolate the obtained mixed nanocrystals using standard techniques, i.e. in analogy as described above (4$^{th}$ aspect). The isolated mixed nanocrystals may be used in similar applications as corresponding known materials, e.g. as described below (8$^{th}$ aspect). Alternatively, the obtained suspension containing pure nanocrystals may be used to prepare capped nanocrystals as described below (e.g. according to the 6$^{th}$ aspect); to prepare a formulation or to prepare a device as described below (e.g. according to the 7$^{th}$ aspect).

In a sixth aspect, the invention relates to the manufacture of capped nanocrystals as described herein. Thus, the invention provides also a process for manufacturing capped nanocrystals as defined herein comprising the steps of
a. Providing a reaction environment comprising a reaction vessel and optionally a vapor phase ballast vessel connected thereto via the gas phase;
b. Providing a suspension ("suspension D"), said suspension comprising pure or mixed nanoparticles as described herein, optionally one or more reaction aids;
c. Providing a solution ("solution E"), said solution comprising a ligand or ligand precursor, solvent, optionally reaction aids and optionally a further solution ("solution F"), said solution comprising reaction aids and solvent d. optionally providing a third solution ("solution C"), said solution comprising solvent and an effective amount of glycerol;

e. Filling the VPB vessel—if present—with solution C and the reaction vessel with suspension D;

f. Adding solution E and optionally solution F to the reaction vessel whereby all steps may be performed under ultra-clean conditions; and whereby the pressure may be maintained below atmospheric pressure. Upon addition of solution C and optionally D to the reaction vessel, the inventive capped nanocrystals are formed.

The process as set out in this aspect of the invention provides homogeneously sized, homogeneously shaped, capped nanocrystals of one or more elements selected from group 3-group 12 of the periodic table of elements which are partly or fully, preferably fully, coated by a layer of ligands. The process provided herein is high yielding and provides improved crystals (e.g. biocompatibility) when compared with the prior art processes. The invention thus also provides a process as described herein characterized by a chemical yield >90 wt. %, preferably >95 wt. %, much preferably >99% of the inventive capped nanocrystals.

This aspect of the invention shall be explained in further detail below. Generally speaking, the manufacturing process of this embodiment differs from the previously described process ($4^{th}$ and $5^{th}$ aspect) in that an additional reaction step (addition of solutions E and optionally F) is performed to obtain capped nanocrystals.

Reaction Conditions:

Reaction conditions are similar to those according to the $4^{th}$ aspect of the invention.

Step a:

Reaction environment: In general, the equipment used is similar to the equipment as describe above, 4th aspect. For handling solutions E and F, additional equipment ("injectors") is required. Generally all reactions are continuously stirred at ca. 200 RPM, maintained under an inert Argon atmosphere at $\leq 10^{-1}$ torr at 60° C.

Step b, c, d, e, f:

These steps are performed in analogy to standard procedures in synthetic chemistry and/or in line with the steps described above ($4^{th}$, $5^{th}$ aspect) and are thus known to the person skilled in the art.

Step c:

It is apparent that the method used in this step strongly depends on the ligand(s) chosen. For example, sulfhydryl groups in Glutathione facilitate crosslinking to surface metals; Carboxylate groups of acids likewise promote crosslinking.

Step d:

It was found advantageous to include glycerol in solution C. Advantageously, an aqueous solution comprising water and 1-10% (v/v), such as 3% (v/v)glycerol, is used.

Step g:

Upon addition of solution B and suspension D to the reaction vessel, the inventive mixed nanocrystals are formed, whereby the nanocrystals of suspension D form said inner crystal(s) and the metal precursor of solution A forms said outer crystal. It was found advantageously to add both, B and D, simultaneously to the reaction vessel. It is understood that B and D are prepared and maintained separately until added to this step g.

Work-Up:

In principle, it is possible to isolate the obtained capped nanocrystals using standard techniques, i.e. in analogy as described above ($4^{th}$ aspect). The isolated capped nanocrystals may be used in similar applications as corresponding known materials, e.g. as described below ($8^{th}$ aspect).

Alternatively, the obtained suspension containing capped nanocrystals may be used to prepare a formulation or to prepare a device as described below (e.g. according to the $7^{th}$ aspect).

In an advantageous embodiment, the present invention relates to a process for manufacturing capped nanocrystal using the pure nanocrystals as described herein as starting material. Thus, the invention also relates to a process for manufacturing capped nanocrystals as defined herein comprising the steps of a. Providing a reaction environment comprising a reaction vessel and a vapor phase ballast vessel connected thereto via the gas phase;

b. Providing a first solution ("solution A"), said solution comprising one or more metal precursors, solvent, optionally one or more reaction aids;

c. Providing a second solution ("solution B"), said solution comprising a reducing agent, solvent, optionally reaction aids d. Providing a third solution ("solution C"), said solution comprising one or more metal precursors, solvent, optionally one or more reaction aids.

e. Providing a further solution ("solution E"), said solution comprising a ligand or ligand precursor, solvent, optionally reaction aids and optionally providing a further solution ("solution F"), said solution comprising reaction aids and solvent;

f. Filling the VPB vessel with solution C and the reaction vessel with solution A;

g. Adjusting the pressure of the reaction environment below atmospheric pressure;

h. Adding solution B to the reaction vessel;

i. Adding solution E and optionally solution F to the reaction vessel;

whereby all steps are performed under ultra-clean conditions; and whereby the pressure is maintained below atmospheric pressure. Upon addition of solution B to the reaction vessel (step h), the pure nanocrystals are formed; upon addition of solution E and optionally F to the reaction vessel (step i), capped nanocrystals are formed.

In an advantageous embodiment, the present invention relates to a process for manufacturing capped nanocrystal using the mixed nanocrystals as described herein as starting material. Thus, the invention also relates to a process for manufacturing capped nanocrystals as defined herein comprising the steps of a. Providing a reaction environment comprising a reaction vessel and a vapor phase ballast vessel connected thereto via the gas phase;

b. Providing a first solution ("solution A"), said solution comprising one or more metal precursors, solvent, optionally one or more reaction aids;

c. Providing a second solution ("solution B"), said solution comprising a reducing agent, solvent, optionally reaction aids and a suspension ("suspension D") said suspension comprising pure nanocrystals as defined herein, solvent, optionally one or more reaction aids;

d. Providing a third solution ("solution C"), said solution comprising one or more metal precursors, solvent, optionally one or more reaction aids.

e. Providing a further solution ("solution E"), said solution comprising a ligand or ligand precursor, solvent, optionally reaction aids and optionally providing a further solution ("solution F"), said solution comprising reaction aids and solvent;

f. Filling the VPB vessel with solution C and the reaction vessel with solution A;
g. Adjusting the pressure of the reaction environment below atmospheric pressure;
h. Adding solutions B and suspension D to the reaction vessel;
i. Adding solution E and optionally solution F to the reaction vessel;
whereby all steps are performed under ultra-clean conditions; and whereby the pressure is maintained below atmospheric pressure. Upon addition of solution B and suspension D to the reaction vessel (step h), the mixed nanocrystals are formed; upon addition of solution E and optionally F to the reaction vessel (step i), capped nanocrystals are formed.

In a seventh aspect, the invention relates to devices and formulations containing pure, mixed and/or coated nanocrystals as described herein.

In one embodiment, the invention provides a device comprising a charged substrate coated with a self-assembled monolayer of pure or mixed nanocrystals as described herein. Suitable charged substrates are known in the field and include materials selected from the group consisting of metallic and non-metallic materials, such as carbon, silicon, platinum, germanium, copper, gold, chromium, tungsten, nickel, scandium, gadolinium, silver and aluminum.

In a further embodiment, the invention provides a suspension comprising a diluent and nanocrystals as described herein. Suitable diluents are known in the field, preferably aqueous systems, such as water.

In an eight aspect, the invention relates to the use of nanocrystals (pure, mixed, coated), formulations and devices as described herein in biomedical applications and/or in material science.

The inventive nanocrystals, formulations and devices are useful in a wide variety of applications, including a) the use as a non-toxic contrast media; b) the use in non-invasive biomedical imaging modes (particularly PET and SPECT); c) in non-invasive cancer diagnostics; d) the use for the treatment, prevention and/or delay of progression of cancer; e) the use for the manufacturing of a pharmaceutical for the treatment, prevention and/or delay of progression of cancer; and f) the use as functional material. This aspect of the invention shall be explained in further detail below:

In one embodiment, the invention provides the use of nanocrystals, particularly functionalized nanoparticles as non-toxic contrast media e.g. for use in in vitro biomedical research, in vitro biomedical diagnostics, in vivo biomedical diagnostics. For example, assays of DHLA and GSH-surface capped nanoparticles exhibit high biocompatibility and greatly increased visible and fluorescent signals with augmented electron-density that amplifies X-ray, CT and ultrasound signals as well. These parameters define use of these particles in next-generation contrast media. Variation of metals produces a different signal signature, i.e., magnetic (such as FeCo@Au), x-ray (such as . . . Au@Fe), or fluorescence (such as Fe@Au).

In one further embodiment, the invention provides the use of isotope [metal] doped mixed nanocrystals (i) in non-invasive biomedical imaging modes (particularly PET and SPECT), (ii) in cancer therapeutics and (iii) in cancer diagnostics. The above described LPSP protocol provides a means to stochiometrically dose isotopes in individual particle sols, thus accurately dosing the diagnostic or therapeutic compound in a well defined delivery vehicle.

Figure 5:
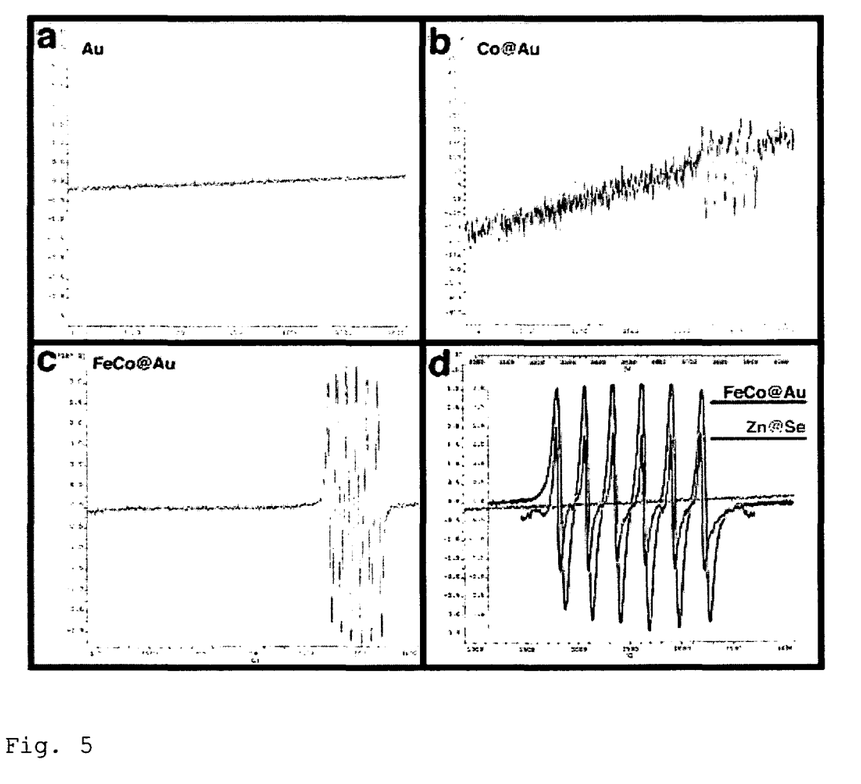

In one further embodiment, the invention provides the use of mixed nanocrystals, particularly magnetic (such as ferromagnetic and/or superparamagnetic) mixed nanocrystals as functional materials, e.g., magnetic RAM (MRAM), optoelectronics, computer chip microcomponents and is integral substrates in automated assays, e.g., affinity arrays and high throughput screening in biomedical research and diagnostics, e.g., MRI. These uses are supported by the ability of such crystals to form self-assembling monolayers. Serial electron paramagnetic resonance EPR spectra display the evolution of clearly defined and elevated ferromagnetic and superparamagnetic spectra of near-absolute yields in raw particle sols in FIG. 5.

In a further embodiment, the present invention provides nanocrystals as described herein, as pharmaceutical, particularly for the treatment of cancer.

To further illustrate the invention, the following examples are provided. These examples are provided with no intent to limit the scope of the invention General/Glass Environment Preparation:

The reaction is performed in a Schlenk-line device as shown in FIG. 6.

All media/chemicals are degassed and kept in desiccators under Argon Ar(g) [Pangas] grade >5. All glassware is acid washed with fresh Aqua Regia, and rinsed with 3D H2O prior to oven drying and use. All 3D $H_2O$ distilled in glass on-site, i.e., no contact with other material. All material and reactions are maintained and carried out in glass attached directly to an all-glass high-vacuum Schlenk line with vacuum drawn through a filtered/gated two-stage "dry" turbo-molecular pump fitted with a liquid Nitrogen LN2 trap. Three pressure gauges provide localized readouts at pre-gated, first and final stages. Apparatus is evacuated to $>10^{-3}$ atm. and purged thrice prior to use. Ultraclean working surfaces and volumes as well as accurate/precise regulation of pressure and temperature are maintained for reproducible control of size and shape of particles.

Maintenance of the following physical, chemical and mechanical parameters is necessary for successful production of homogenously sized and shaped 3D nanoparticles.

EXAMPLE 1

Pure Nanocrystals (Au)

The reaction vessel is filled with a 100 ml aqueous solution containing 1% (w/v) HAuCl4 (tetraaurochloric acid).

The VPB vessel is filled with a similar volume of triple distilled water and 1% (w/v) Tannic acid 2 ml 1% (w/v)tri-sodium citrate-2H2O.

To the reaction vessel is added under inert Argon atmosphere at $\leq 10^{-1}$ torr while stirring a solution preheated to 60° C. containing 4 ml 1% tri-sodium citrate-2H2O+16 ml H2O+5 ml of 1% tannic acid.

After a brief color change (red) a suspension of trigonal pyramidal Au nanoparticles is obtained.

EXAMPLE 2

Pure Nanocrystals (Fe)

Similarly to ex. 1, pure Fe nanocrystals are obtained using FeCl3 and FeCl2 as starting materials.

The reaction vessel is filled with 200 ml triple distilled H2O containing 14.6 g FeCl3:6H2) and 5.7 g FeCl2:4H2O.

The VPB vessel is filled with a similar volume of triple distilled water and 1% (w/v) tannic acid 2 ml 1% (w/v)tri-sodium citrate-2H2O.

To the reaction vessel is added under inert Argon atmosphere at $\leq 10^{-1}$ torr while stirring a solution preheated to 60° C. containing 4 ml 1% tri-sodium citrate-2H2O+16 ml H2O+5 ml of 1% tannic acid. The solution is stirred continuously maintained at 60° C. The temperature is raised to 90° C. for another hour. A suspension of hexagonal pyramidal nanoparticles is obtained.

EXAMPLE 3

Pure Nanocrystals (FeCo)

The reaction vessel is filled with a solution containing 200 ml 3 mM tannic acid solution and 50 ml of 10 mM CoCl2 and heated to 60° C. 5 ml 2N HCl is added to 25 ml 220 mM FeCl3:6 H2O heated to 60° C. and added to reaction vessel under constant stirring.

The VPB vessel is filled with 300 ml of 76 mM FeC6H5O7.

To the reaction vessel under inert Argon atmosphere at ≤0.1 torr is added an aqueous solution containing 40 ml 10 mM lipoic acid, 25 ml 30 mM Glutathione, 40 ml of 38 mM tri-sodium citrate and 100 ml 3 mM tannic acid under stirring.

The reaction is heated to 90° C. for 30 minutes and a suspension of FeCo nanoparticles is obtained.

EXAMPLE 4

Mixed Nanocrystals (FeCo Inside Au)

Stage 1
Solution A: 5 ml 2N HCl is added to 25 ml 220 mM FeCl3:6[H2O] (aq) pre-heated to 60° C. and added to a solution preheated to 60° C. containing 50 ml of 10 mM CoCl2 and 200 ml stock 3 mM C76H52O46 in a 1000 ml triple-neck RBF fitted with a motorized glass stir rod drawn through sealed septum, pre-evacuated and flooded with Ar. This mixture is stirred at ca. 200 RPM maintained under inert Argon atmosphere at ≤0.1 torr at 60° C.
Solution B: 1 ml stock 30 mM HAuCl4 is added to 99 ml 3D H2O in a 250 ml flat-bottomed RBF [Schott] evacuated, Ar flooded and placed in 60° C. waterbath.
Solution C: 40 ml 10 mM C8H14O2S2 and 25 ml 30 mM C10H17N3O6S are added under Ar to 40 ml of 38 mM C6H5Na3O7 and 100 ml 3 mM C76H52O46 in a 250 ml flat-bottomed RBF [Schott] evacuated, Ar flooded and heated to 60° C. in waterbath.
Stage 2
100 ml of Solution C is pipetted into a calibrated glass pipette evacuated and flooded with Ar and injected under Ar into Solution A while stirring. The combined co-reductants of glutathione [GSH], tannic acid [TA] and tri-sodium citrate, promote a relatively slow stepwise formation of primary crystals leading to a homogenous suspension of primary particles. Color change observed yellow to red to dark blue. Mixture is allowed to reach equilibria at 60° C. 100 ml Solution B is then drawn in an Ar flooded glass pipette and injected under inert Argon atmosphere at ≤0.1 torr to Solution A/C under stirring. Witness a color change to light purple. Heat to reflux 10 min while stirring.

EXAMPLE 5

Mixed Nanocrystals (Fe Inside Au)

Stage 1
Solution A: 1 ml stock 30 mM HAuCl4 is added to 99 ml 3D H2O and 100 ml 0.1 M (CH3)2AsOOH preheated to 60° C. a 1000 ml triple-neck RBF fitted with a motorized glass stir rod drawn through sealed septum, pre-evacuated and flooded with Ar. This mixture is stirred at ca. 200 RPM maintained under inert Argon atmosphere at ≤0.1 torr at 60° C. Pale gold to clear pale yellow color change.
Solution B: 5 ml 2N HCl is added to 95 ml 84 mM FeCl3:6 [H2O] (aq) and 10 ml of 1.0 M NH4NCS in a 250 ml flat-bottomed RBF [Schott] evacuated, Ar flooded and placed in 60° C. water bath.
Solution C: Stock Yeast Casitone Fatty Acid Media: As prepared dry: (per 100 ml liquid final concentration) 1.0 g casitone, 0.25 g yeast extract, 0.4 g NaHCO3, 0.1 g cysteine, 0.045 g K2HPO4, 0.045 g KH2PO4, 0.09 g NaCl, 0.009 g MgSO4.7H2O, 0.009 g CaCl2, 1 mg haemin, 1 µg biotin, 1 µg cobalamin, 3 µg p-aminobenzoic acid, 5 µg folic acid and 15 µg pyridoxamine. Final concentrations of short-chain fatty acids (SCFA) in the medium were 33 mM acetate, 9 mM propionate and 1 mM each of isobutyrate, isovalerate and valerate.
Stage 2
100 ml YCFA Solution C is pipetted into Solution A in the 1000 ml RBF under Ar under constant stirring at 60° C.
20 ml of Solution B/ is [injected] pipetted rapidly under Ar while stirring is maintained at 60° C. This [CAB] mixture is heated to boil (ca. 110° C.) and permitted to reflux 25 minutes. Color change from clear pale yellow to brownish red. A suspension of hexagonal pyramdal Fe nanoparticles inside trigonal Au pyramids is obtained.

EXAMPLE 6

Capped Nanoparticles (Au Coated with DHLA+GSH)

The reaction vessel is filled with as solution containing 1 ml of 1% HAuCl4 in 99 ml H2O stirred at ca. 200 RPM, maintained under inert Argon atmosphere at ≤0.1 torr at 60° C.

The VPB vessel is filled with 130 ml H20, 5 ml 1% (w/v) tannic acid, 5 ml 30 mM glutathione, 12 ml 10 mM lipoic acid, 4 ml 1% (w/v) tri-sodium citrate: 2H2O.

To the reaction vessel is added as solution containing 5 ml 30 mM glutathione, 12 ml 10 mM lipoic acid, 4 ml 1% (w/v) tri-sodium citrate: 2H2O+16 ml H2O+2 ml of 1% (w/v) tannic acid.

After raising the temperature to reflux for 10 min, a suspension of trigonal pyramidal Au nanoparticles coated with DHLA and GSH is obtained.

EXAMPLE 7

Capped Nanoparticles (Fe Coated with GSH)

The reaction vessel is filled with as solution containing 100 ml of pure hexagonal pyramidal iron nanocrystals (prepared as in example 2 above).

The VPB vessel is filled with 120 ml H2O.

To the reaction vessel stirred at ca. 200 RPM, maintained under inert Argon atmosphere at ≤0.1 torr at 60° C. is added as solution containing 5 ml 30 mM glutathione, 12 ml 10 mM lipoic acid, 4 ml 1% (w/v) tri-sodium citrate: 2H2O+16 ml H2O+2 ml of 1% (w/v) tannic acid.

Figure 1:
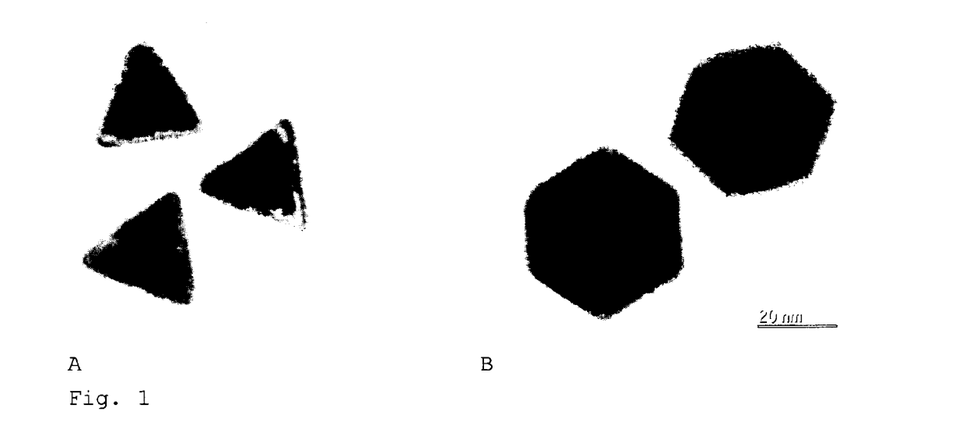
FIG. 1 shows pure nanocrystals according to this invention, whereby 1 A shows an assembly of trigonal pyramidal Au nanoparticles; 1 B shows an assembly of hexagonal pyramidal Fe nanoparticles.
Figure 2:
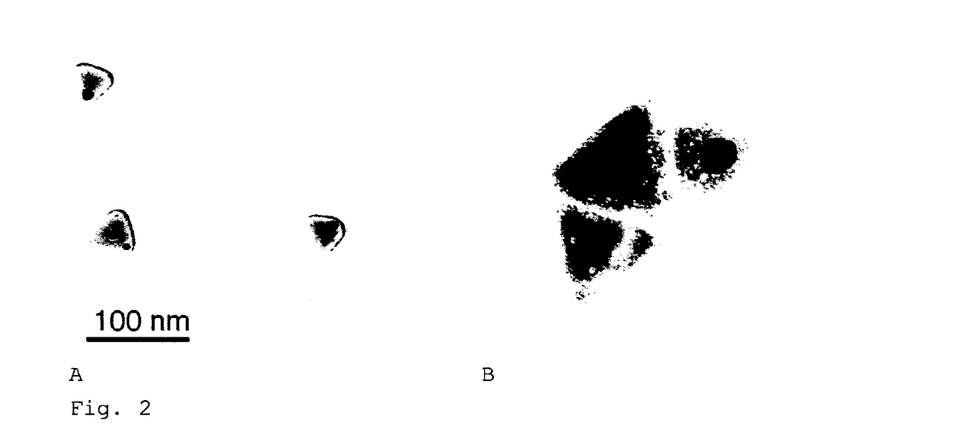
FIG. 2 shows mixed nanocrystals according to this invention, whereby 2 A shows hexagonal pyramidal FeCo inside trigonal pyramidal Au nanoparticles; 2 B shows Fe hexagonal crystal cores inside Au trig. pyramids.
Figure 3:
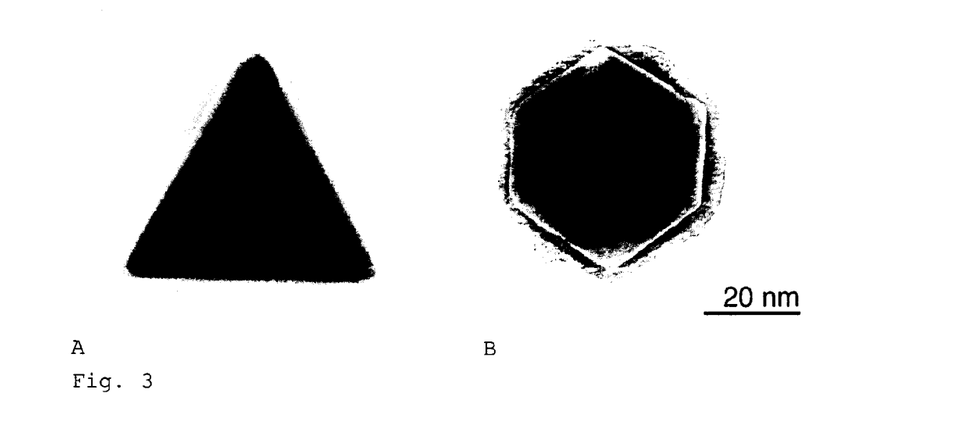
FIG. 3 shows capped nanocrystals according to this invention, whereby 3 A shows trigonal pyramidal Au nanoparticles coated with DHLA and GSH; 3 B shows hexagonal pyramidal Fe nanoparticles coated with GSH.
Figure 4:
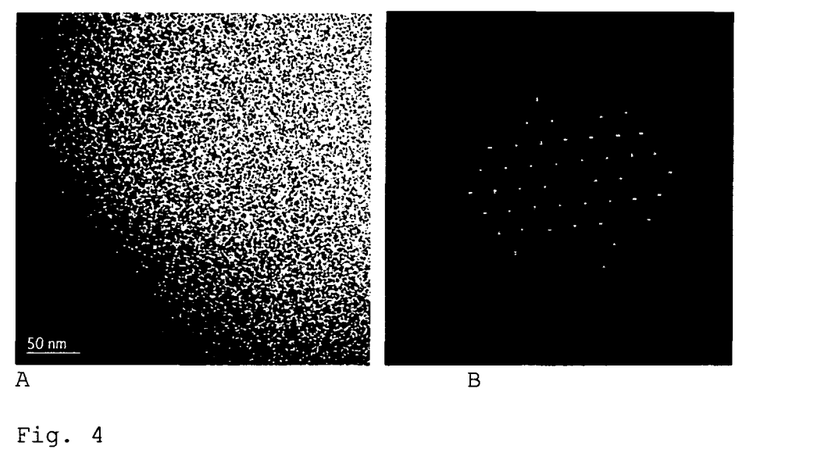
FIG. 4 shows an assembly of Au@Fe nanocrystals, whereby 4 A shows a self-assembled monolayer of crystals, 4 B shows coherent electron beam X-ray diffraction of the selection in 4A.

The reaction is heated to 70° C. and a suspension of hexagonal pyramidal Fe nanoparticles coated with GSH is obtained; see FIG. 1B, FIG. 3B.

In an additional example, the reaction was carried out in the absence of a VPB; the material obtained showed essentially the same characteristics.

EXAMPLE 8

Pure Nanocrystals ($^{198}$Au)

Similarly to ex. 1, pure radioisotope-doped nanocrystals are obtained using H$^{198}$AuCl4 as starting materials After a brief color change (red) a suspension of trigonal pyramidal $^{198}$Au nanoparticles, are obtained. Reaction conditions were chosen to obtain particles of either 5 nm or 40 nm. Chemical yields are above 90 wt. %, determined by ICP-MS.

EXAMPLE 9

Pure Nanocrystals ($^{57}$Fe)

Similarly to ex. 8, radioisotope-doped nanocrystals are obtained using $^{57}$FeCl3 as starting materials.

A suspension of hexagonal pyramidal $^{57}$Fe nanoparticles, 10 nm, is obtained. Chemical yields are above 90 wt. %, determined by ICP-MS.

Analytical Studies:

Ion-Coupled Plasma Mass Spectroscopy [ICP-MS] elemental analysis of single and mixed metal sols and X-ray dispersive [XRDS] and electron-energy loss spectroscopy [EELS] of individual particles reflects the following concentrations, stochiometric ratios and yields of individual metal species. ICP-MS is considered an exact analytical method, while EELS and XRDS are considered quantitative and semi-quantitative respectively.

1. The average metal content by ICP-MS analysis of four single metal gold (Au) sols was 76 micrograms Au per milliliter. This suggests a near absolute yield of pure nanocrystals according to ex. 1 from initial Tetraaurochloric Acid [HAuCl$_4$] concentration of 80 micrograms per milliliter, i.e., ≥94%.
2. EELS and XRDS analysis of individual mixed metal nanocrystals (Fe inside Au, according to ex. 5, n=17) displayed a 1 to 4 ratio of iron to gold.
3. Comparable results are obtained for examples 2-4, 6-9.

The invention claimed is:

1. A method for manufacturing an assembly of nanocrystals, ("pure nanocrystals"), said method comprising the steps of:
   (a) providing a reaction environment comprising a reaction vessel and a vapor phase ballast vessel connected thereto via the gas phase;
   (b) providing a first solution ("solution A"), said solution comprising one or more metal precursors, solvent, optionally one or more reaction aids;
   (c) providing a second solution ("solution B"), said solution comprising a reducing agent, solvent, optionally reaction aids;
   (d) providing a third solution ("solution C"), said solution comprising reducing agent(s), solvent, and optionally reaction aids;
   (e) filling the vapor phase ballast vessel with solution C and the reaction vessel with solution A; and
   (f) adjusting the pressure of the reaction environment below atmospheric pressure;
   (g) adding solutions B to the reaction vessel;
   whereby all steps are performed under ultra-clean conditions;
   whereby the pressure is maintained below atmospheric pressure;
   whereby the method is performed in aqueous medium; and
   wherein each nanocrystal of the assembly of nanocrystals contains one metal of group 1-12 metals of the periodic table of elements, has a size of 2 to 200 nm, and has a defined, three-dimensional polyhedral structure, being free of, or essentially free of, lattice defects.

2. A method for manufacturing an assembly of nanocrystals, ("mixed nanocrystals"), said method comprising the steps of:
   (a) providing a reaction environment comprising a reaction vessel and a vapor phase ballast vessel connected thereto via the gas phase;
   (b) providing a first solution ("solution A"), said solution comprising one or more metal precursors, solvent, optionally one or more reaction aids;
   (c) providing (i) second solution ("solution B"), said solution comprising a reducing agent, solvent, and optionally reaction aids; and (ii) a suspension ("suspension D"), said suspension comprising pure nanocrystals, solvent, and optionally one or more reaction aids, wherein each pure nanocrystal contains one or more metals, at least one of which is a metal of group 1 to 12 of the periodic table of elements; has a size of 2 to 200 nm; and has a defined, three-dimensional polyhedral structure, being free of, or essentially free of, lattice defects, the nanocrystal being free of ligands;
   (d) providing a third solution ("solution C"), said solution comprising reducing agent(s), solvent, and optionally reaction aids;
   (e) filling the vapor phase ballast vessel with solution C and the reaction vessel with solution A;
   (f) adjusting the pressure of the reaction environment below atmospheric pressure; and
   (g) adding solutions B and suspension D to the reaction vessel;
   whereby all steps are performed under ultra-clean conditions;
   whereby the pressure is maintained below atmospheric pressure;
   whereby the method is performed in aqueous medium; and
   wherein each mixed nanocrystal of the nanocrystal assembly contains one or more inner nanocrystals surrounded by an outer nanocrystal; whereby said inner nanocrystals contain one or more metals of group 1 to 12 of the periodic table of elements; have a size of 1 to 100 nm; have a defined, three-dimensional polyhedral structure; and whereby said outer nanocrystal contains one or more elements of group 1 to 12 of the periodic table of elements; has a size of 3 to 200 nm; has a defined, three-dimensional polyhedral structure; and whereby the elements of inner and outer crystal differ.

3. A method for manufacturing an assembly of nanocrystals, ("capped pure nanocrystals"), said method comprising the steps of:
   (a) providing a reaction environment comprising a reaction vessel and a vapor phase ballast vessel connected thereto via the gas phase;
   (b) providing a suspension ("suspension D"), said suspension comprising pure nanoparticles, and optionally one or more reaction aids, wherein each nanocrystal contains one or more metals, at least one of which is a metal of group 1 to 12 of the periodic table of elements; has a size of 2 to 200 nm; and has a defined, three-dimensional polyhedral structure, being free of, or essentially free of, lattice defects, the nanocrystal being free of ligands;
   (c) providing a solution ("solution E"), said solution comprising a ligand or ligand precursor, solvent, optionally reaction aids and optionally a further solution ("solution F"), said solution comprising reaction aids and solvent;

(d) optionally providing a third solution ("solution C"), said solution comprising reducing agent(s), solvent, and optionally reaction aids; and (e) filling the vapor phase ballast vessel with solution C, if present, and the reaction vessel with suspension D;

(f) adding solution E and optionally solution F to the reaction vessel;

whereby all steps are performed under ultra-clean conditions;

whereby the pressure is maintained below atmospheric pressure;

whereby the method is performed in aqueous medium; and wherein each nanocrystal of the assembly of nanocrystals contains one metal of group 1-12 metals of the periodic table of elements, has a size of 2 to 200 nm, and has a defined, three-dimensional polyhedral structure, being free of, or essentially free of, lattice defects, and further contains ligands that partly or fully cover the surface of said nanocrystals.

4. A method for manufacturing an assembly of nanocrystals, ("capped mixed nanocrystals"), said method comprising the steps of:

(g) providing a reaction environment comprising a reaction vessel and a vapor phase ballast vessel connected thereto via the gas phase;

(h) providing a suspension ("suspension D"), said suspension comprising mixed nanoparticles, and optionally one or more reaction aids, wherein each mixed nanocrystal contains one or more inner nanocrystals surrounded by an outer nanocrystal, the inner nanocrystal(s) contain one or more metals of group 1 to 12 of the periodic table of elements, have a size of 1 to 100 nm, and have a defined, three-dimensional polyhedral structure; and the outer nanocrystal contains one or more elements of group 1 to 12 of the periodic table of elements, has a size of 3 to 200 nm and has a defined, three-dimensional polyhedral structure; and whereby the elements of inner and outer crystal differ, the nanocrystal being free of ligands;

(i) providing a solution ("solution E"), said solution comprising a ligand or ligand precursor, solvent, optionally reaction aids and optionally a further solution ("solution F"), said solution comprising reaction aids and solvent;

(j) optionally providing a third solution ("solution C"), said solution comprising reducing agent(s), solvent, and optionally reaction aids; and (k) filling the vapor phase ballast vessel with solution C, if present, and the reaction vessel with suspension D;

(l) adding solution E and optionally solution F to the reaction vessel;

whereby all steps are performed under ultra-clean conditions;

whereby the pressure is maintained below atmospheric pressure;

whereby the method is performed in aqueous medium; and wherein each mixed nanocrystal of the nanocrystal assembly contains one or more inner nanocrystals surrounded by an outer nanocrystal; whereby said inner nanocrystals contain one or more metals of group 1 to 12 of the periodic table of elements; have a size of 1 to 100 nm; have a defined, three-dimensional polyhedral structure; and whereby said outer nanocrystal contains one or more elements of group 1 to 12 of the periodic table of elements; has a size of 3 to 200 nm; has a defined, three-dimensional polyhedral structure; and whereby the elements of inner and outer crystal differ, and the mixed nanocrystals further contain ligands that partly or fully cover the surface of said nanocrystals.

* * * * *

UNITED STATES PATENT AND TRADEMARK OFFICE
CERTIFICATE OF CORRECTION

PATENT NO.         : 8,871,182 B2
APPLICATION NO.    : 13/697395
DATED              : October 28, 2014
INVENTOR(S)        : Christophe Jan Lacroix et al.

It is certified that error appears in the above-identified patent and that said Letters Patent is hereby corrected as shown below:

Title Page, Item (73), Assignee,
"Eth Zurich" should be -- ETH Zurich --.

Signed and Sealed this
Tenth Day of February, 2015

Michelle K. Lee
*Deputy Director of the United States Patent and Trademark Office*